United States Patent [19]

Dye

[11] 4,013,310
[45] Mar. 22, 1977

[54] TUBING CONNECTOR

[75] Inventor: John F. Dye, Reedsburg, Wis.

[73] Assignee: The Kendall Company, Boston, Mass.

[22] Filed: July 29, 1976

[21] Appl. No.: 709,742

Related U.S. Application Data

[63] Continuation of Ser. No. 594,379, July 9, 1975, abandoned.

[52] U.S. Cl. .............................. 285/110; 285/177; 285/319; 285/322; 285/423
[51] Int. Cl.² ........................................ F16L 17/02
[58] Field of Search .......... 285/110, 322, 225, 345, 285/423, 255, 243, 323, 324, 319, 315, 316, 177, 423; 128/247

[56] References Cited

UNITED STATES PATENTS

| 613,903 | 11/1898 | Hussey | 285/322 X |
|---|---|---|---|
| 1,001,069 | 8/1911 | Nielsen | 285/322 X |
| 2,032,297 | 2/1936 | Mikulasek | 285/243 |
| 2,383,692 | 8/1945 | Smith | 285/322 |
| 2,531,401 | 11/1950 | Clerke | 285/322 |
| 2,702,716 | 2/1955 | Basolo et al. | 285/322 |
| 2,784,987 | 3/1957 | Corcoran | 285/322 X |

FOREIGN PATENTS OR APPLICATIONS

| 89,469 | 10/1960 | Denmark | 285/110 |
|---|---|---|---|
| 572,729 | 2/1924 | France | 285/322 |
| 1,435,463 | 3/1966 | France | 285/110 |
| 105,554 | 7/1924 | Switzerland | 285/110 |
| 975,743 | 11/1964 | United Kingdom | 285/322 |

Primary Examiner—Thomas F. Callaghan
Attorney, Agent, or Firm—Powell L. Sprunger

[57] ABSTRACT

A device for connecting a tube comprising, a housing having a passageway to receive the tube, and a flexible diaphragm having an opening of a size to receive and frictionally engage an outer surface of the tube. The diaphragm is retained in the housing with the opening aligned with the passageway, and the device has means for retaining the tube in the housing with the tube extending through the diaphragm.

9 Claims, 4 Drawing Figures

TUBING CONNECTOR

This is a continuation of application Ser. No. 594,379, filed July 9, 1975, and now abandoned.

BACKGROUND OF THE INVENTION

The present invention relates to connectors, and more particularly to connectors for tubes.

In numerous medical procedures it is necessary to connect tubes to a separate object or another tube, such as, for example, a procedure during which a tube is connected to a wound suction device. Particularly in the case of a tube with a relatively small diameter, it is often difficult to make the connection in a simple and efficient manner. In the past, the connection has often been accomplished by inserting the short tip of a small hypodermic needle into the tube, and by then connecting the needle to the device or another tube through use of a luer adapter. However, since the needle tip which is positioned within the tube reduces its internal diameter, the tip effectively acts as a restriction against passage of fluid through the lumen of the tube, and the needle tip may break through the tube wall during later use thus causing a leak. Additionally, the needle tip should have a blunt end, thus requiring a non-standard needle, which, due to its relatively small size, may be easily lost or dropped resulting in contaminating of the needle. If the outside diameter of the needle tip is too large relative the tube, the tip may tear the tubing while making the connection, and if too small, the connection may leak between the tube and tip during use. Even if the needle tip has the correct size, it has been found difficult to insert the needle into the relatively small tube without puncturing the tube.

SUMMARY OF THE INVENTION

A principal feature of the present invention is the provision of a device for connecting a tube to another object or tube in a simple and efficient manner.

The device of the present invention comprises, a housing having a passageway to receive the tube, and a flexible diaphragm having an opening of a size to receive and frictionally engage an outer surface of the tube. The diaphragm is retained in the housing with the opening aligned with the passageway, and the device has means for retaining the tube in the housing with the tube extending through the diaphragm.

A feature of the present invention is that the tube may be readily inserted into the passageway and through the diaphragm opening in order to position the tube within the housing.

Another feature of the invention is that the diaphragm sealingly engages against an outer surface of the tube, and does not restrict passage of fluid through the tube lumen.

Still another feature of the invention is that the retaining means may be utilized to releasably lock the tube within the housing with the tube extending through the diaphragm.

Thus, a feature of the present invention is that the tube may be readily positioned and locked in place within the connecting device.

Yet another feature of the invention is that a variable length of the tube may be connected in the device, and the device may be used to reduce slack in the tube.

Another feature of the invention is that the tube may be readily unlocked and removed from the connecting device without damage to the tube.

Further features will become more fully apparent in the following description of the embodiments of this invention and from the appended claims.

DESCRIPTION OF THE PREFERRED EMBODIMENTS

Figure 1:
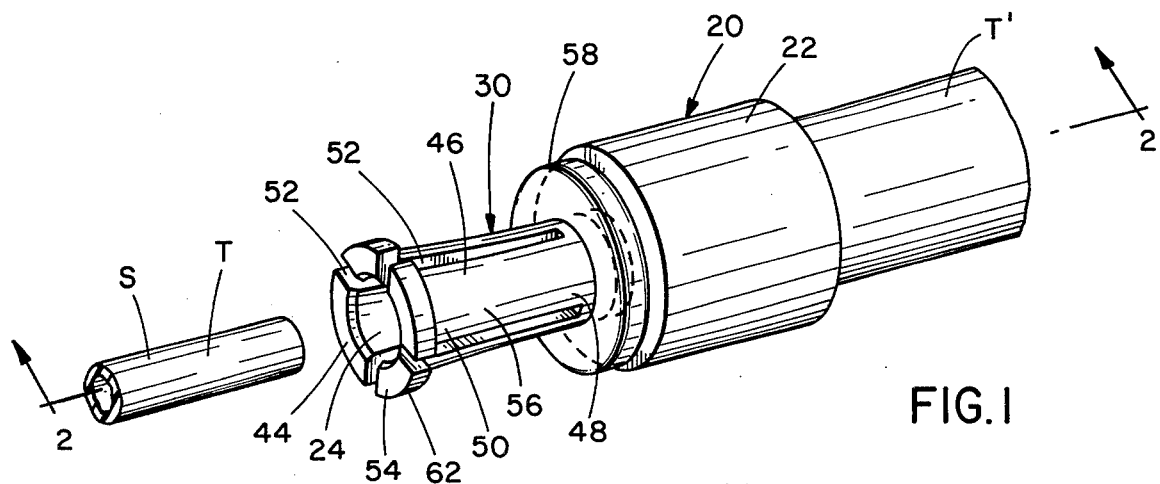
FIG. 1 is a perspective view of a connecting device of the present invention.
Figure 2:
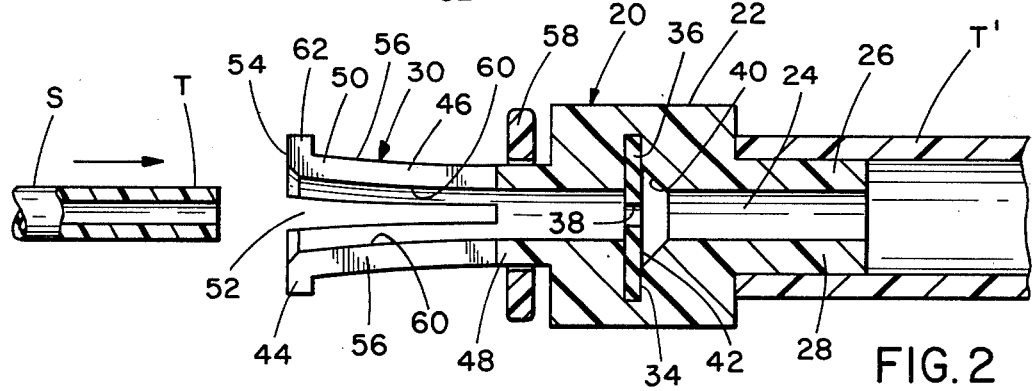
FIG. 2 is a sectional view of the device of FIG. 1 showing a tube being inserted into a passageway of a housing.

Referring now to FIGS. 1 and 2, there is shown a connecting device generally designated 20 having a housing 22 which has a passageway 24 extending through the housing to receive a tube T. The housing may have a connecting portion 26 adjacent one end 28 of the housing for connecting the housing to a second tube T' or other device communicating with the passageway 24. The housing 22 also has a collet assembly generally designated 30 adjacent the other end 44 of the housing to releasably lock the tube T within the housing.

As shown, the housing 22 has a generally circular recess 34 extending from the passageway 24 to receive a generally circular shaped, flexible diaphragm 36 which may be made of any suitable material, such as rubber. The diaphragm 36 has an opening 38 adjacent the center of the diaphragm, and the lateral midpoint of the passageway 24 is located adjacent the center of the recess 34, such that the diaphragm opening 38 is located adjacent the lateral midpoint of the passageway 24. The housing 22 also has a frustro-conical shaped enlargement 40 of the passageway 24 defining a cutout adjacent a side 42 of the diaphragm 36 remote the other end 44 of the housing or passageway through which the tube T is received.

Figure 3:
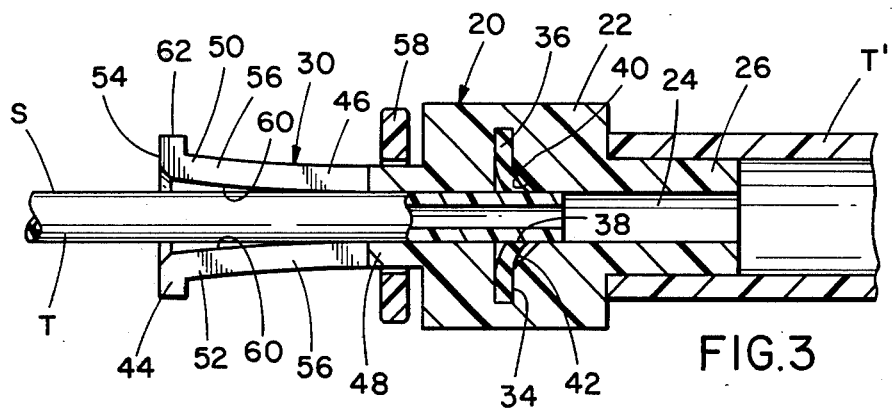
FIG. 3 is a sectional view of the device of FIG. 1 showing the tube being passed through a flexible diaphragm within the housing.
Figure 4:
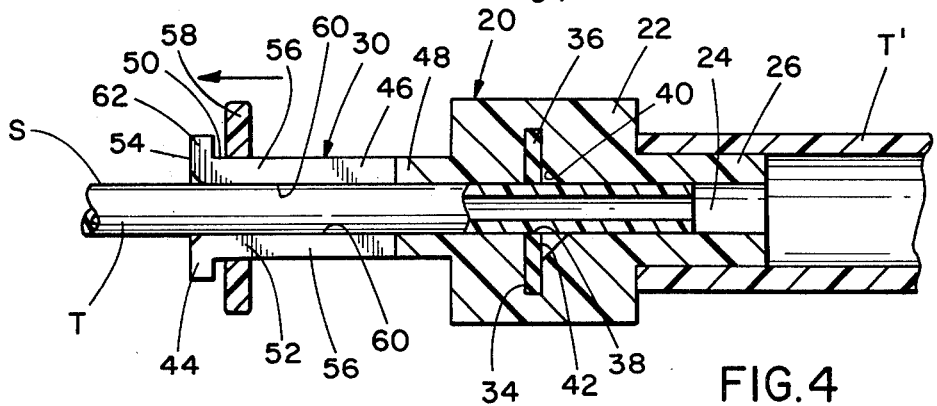
FIG. 4 is a sectional view of the device of FIG. 1 showing the tube being locked in place within the housing by a collet assembly.

The collet assembly 30 is formed in the following manner. The housing 22 has a tubular portion 46 adjacent the other end 44 of the housing, with the tubular portion 46 having a first smaller outer diameter adjacent an inner end 48 of the tubular portion 46 which tapers to an enlarged outer diameter adjacent an outer end 50 of the tubular portion 46. The tubular portion 46 has a plurality of elongated slots 52 extending from an outer end edge 54 of the tubular portion 46, and defining a plurality of flexible gripping members or fingers 56. A collet ring 58 is slidably received on the tubular portion 46, and has an inner diameter slightly larger than the outside diameter at the inner end 48 of the tubular portion 46, and has an inner diameter smaller than the outer diameter of the tubular portion at the outer end 50 of the tubular portion. Thus, as shown in FIG. 3, when the ring 58 is located at the inner end 48 of the tubular portion 46, the gripping members 56 are permitted to flex outwardly and receive the tube T with their inner surfaces 60 spaced from the outer surface S of the tube T. As shown in FIG. 4, when the ring 58 is moved toward the outer end 50 of the tubular portion 46, the inner surface of the ring 58 engages against the outer surfaces of the gripping members 56 and urges the gripping members 56 to an inner configuration with their inner surfaces 60 frictionally engaged against the outer surface S of the tube T to releasably lock the tube T in place within the housing. The tubular portion 46 also has an outwardly directed flange 62 at its outer end to retain the collet ring 58 on the gripping members 56.

In use of the device, the ring 58 is moved to the inner end 48 of the tubular portion 48, as shown in FIG. 2. Next, the tube T is inserted into the other end 44 of the passageway 24 until the tube T passes through the opening 38 of the diaphragm 36, as shown in FIG. 3. The frustro-conical shaped enlargement 40 permits flexation of the diaphragm away from the tube T as it passes through the opening 38 to permit easy placement of the tube T within the diaphragm opening 38. The user may move the tube T through the diaphragm 38 to select the distance which the tube T extends into the housing, as desired, in order to reduce slack in the tube T. After the tube T has been positioned in the diaphragm opening 38, the diaphragm is permitted to assume its normal position, as shown in FIG. 4, with the diaphragm sealingly engaging against the outer surface S of the tube T.

Finally, the collet ring 58 is moved toward the outer end 50 of the tubular portion 46 to move the gripping members 56 against the tube T, such that their inner surfaces 60 frictionally engage against the outer surface S of the tube T to releasably lock the tube T within the housing 22 with the tube T passing through the diaphragm 36. In this manner, the tube T is readily connected by the device 20 to the second tube T' without damage to the tube T, and without restricting passage of fluid through the lumen of the tube T. Also, the tube T may be readily disconnected from the device 20 without damage to the tube T by moving the collet ring 58 to the inner end 48 of the tubular portion 46, and by withdrawing the tube T from the diaphragm 36 and the housing 22.

The foregoing detailed description is given for clearness of understanding only, and no unnecessary limitations should be understood therefrom, as modifications will be obvious to those skilled in the art.

I claim:

1. A connection device, comprising:
   a tube having a lumen and an outer surface;
   a housing having a passageway to receive the tube, and a tubular portion adjacent one end of the housing defining an end of the passageway to receive the tube and having an outer surface tapering from a first smaller diameter to a second larger diameter adjacent an outer end edge of the tubular portion, with the remainder of said passageway having a larger internal diameter than the outside diameter of said tube;
   an annular flexible sealing member having an opening of a size to receive and frictionally engage said outer surface of the tube, said sealing member being retained in the housing with the opening aligned with the passageway, whereby an end of the tube may be inserted into the passageway and through the sealing member opening with the sealing member engaging the outer surface of the tube;
   means for retaining the tube in the housing with the tube extending through the sealing member comprising, a plurality of gripping members at the one end of the housing defined by a plurality of elongated slots extending from the end edge of the tubular portion and spaced peripherally around the tubular portion, and a ring slidably received on said tubular portion, with the inner diameter of the ring being greater than said first diameter and less than said second diameter, whereby said ring may be positioned at an inner portion of the tubular portion for inserting the tube into the housing with an inner surface of the gripping members spaced from the outer surface of the tube, and said ring may be moved toward the outer end of the gripping members to flex the gripping members toward the tube and frictionally engage the inner surface of the gripping members against the outer surface of the tube to releasably lock the tube in place within the housing; and
   fluid transmitting means connected to the other end of the housing and having cavity means at least as large as the internal diameter of said remaining portion of the passageway, whereby said tube may be positioned at a selected location in the passageway or positioned with an end portion extending from the passageway into the cavity means in order to reduce slack in said tube.

2. The device of claim 1 wherein said sealing member comprises a diaphragm.

3. The device of claim 1 wherein the diaphragm has a greater width than said passageway, said housing includes an enlarged recess extending from the passageway, and in which outer portions of the diaphragm are received in the recess to retain the diaphragm in place within the housing.

4. The device of claim 3 in which said housing has a cutout adjacent the passageway on a side of the diaphragm remote an end of the passageway through which the tube is received, said cutout permitting flexation of the diaphragm adjacent the diaphragm opening when the tube passes through the diaphragm.

5. The device of claim 1 wherein the diaphragm has a generally circular shape, and the housing includes a generally circular recess extending from the passageway to receive and retain the diaphragm within the housing.

6. The device of claim 5 in which the diameter of the diaphragm is approximately equal to the diameter of the housing recess.

7. The device of claim 5 wherein said opening is located adjacent the center of the diaphragm, and in which the center of the recess is located adjacent the lateral midpoint of the passageway.

8. The device of claim 5 in which the housing includes a frusto-conical enlargement of the passageway adjacent a side of the diaphragm remote an end of the passageway through which the tube is inserted for placement in the housing, said enlargement permitting flexation of the diaphragm when the tube passes through the diaphragm.

9. The device of claim 1 including a second tube secured to an end of the housing, said second tube communicating with the passageway on a side of the sealing member remote an end of the passageway through which the other tube is inserted during placement.

* * * * *